(12) United States Patent
Argañarás et al.

(10) Patent No.: US 10,478,452 B2
(45) Date of Patent: Nov. 19, 2019

(54) ANTIVIRAL PHARMACEUTICAL COMPOSITION FOR TOPICAL USE

(71) Applicant: QUIMICA LUAR SRL, Córdoba (AR)

(72) Inventors: Luis Alberto Argañarás, Córdoba (AR); Roxana Valeria Alasino, Córdoba (AR); Dante Miguel Beltramo, Córdoba (AR)

(73) Assignee: QUIMICA LUAR SRL, Cordoba (AR)

( * ) Notice: Subject to any disclaimer, the term of this patent is extended or adjusted under 35 U.S.C. 154(b) by 0 days.

(21) Appl. No.: 15/573,901

(22) PCT Filed: May 13, 2016

(86) PCT No.: PCT/ES2016/070365
§ 371 (c)(1),
(2) Date: Nov. 14, 2017

(87) PCT Pub. No.: WO2016/185069
PCT Pub. Date: Nov. 24, 2016

(65) Prior Publication Data
US 2018/0250327 A1    Sep. 6, 2018

(30) Foreign Application Priority Data
May 15, 2015   (AR) .............................. P20150101519

(51) Int. Cl.
| A61K 9/06 | (2006.01) |
| A61K 31/78 | (2006.01) |
| A61K 47/20 | (2006.01) |
| A61K 31/167 | (2006.01) |
| A61K 9/00 | (2006.01) |
| A61K 31/4425 | (2006.01) |
(Continued)

(52) U.S. Cl.
CPC ............ *A61K 31/78* (2013.01); *A61K 9/0014* (2013.01); *A61K 9/06* (2013.01); *A61K 31/167* (2013.01); *A61K 31/4425* (2013.01); *A61K 47/20* (2013.01); *A61P 31/22* (2018.01)

(58) Field of Classification Search
None
See application file for complete search history.

(56) References Cited

U.S. PATENT DOCUMENTS

| 3,743,727 A | 7/1973 | Herschler |
| 7,462,369 B2 | 12/2008 | Smith |
| 2005/0003020 A1 | 6/2005 | Smith |
(Continued)

FOREIGN PATENT DOCUMENTS

| EP | 1762226 | 3/2007 |
| WO | 2005074947 | 8/2005 |

OTHER PUBLICATIONS

International Search Report of PCT/ES2016/070365 dated Jul. 8, 2016.
(Continued)

*Primary Examiner* — Ernst V Arnold
*Assistant Examiner* — Kyung S Chang
(74) *Attorney, Agent, or Firm* — Silvia Salvadori

(57) ABSTRACT

The invention relates to an antiviral pharmaceutical composition for topical use against those viruses with a lipid envelope, comprising, as active ingredients a cationic copolymer containing tertiary amine groups and a cationic surfactant containing quaternary ammonium groups.

18 Claims, 1 Drawing Sheet

(51) Int. Cl.
*A61K 31/22* (2006.01)
*A61P 31/22* (2006.01)

(56) References Cited

U.S. PATENT DOCUMENTS

2006/0127487 A1* 6/2006 Verreck .................. A61K 9/146
424/489
2012/0134952 A1* 5/2012 Snyder ................ A61K 31/045
424/78.35
2014/0328895 A1 11/2014 Friedman et al.

OTHER PUBLICATIONS

Research published on International Journal of Pharmaceutical Compounding vol. 4 No. 1 Jan./Feb. 2000.
Written Opinon dated Jul. 8, 2016 for PCT/ES2016/070365.

* cited by examiner

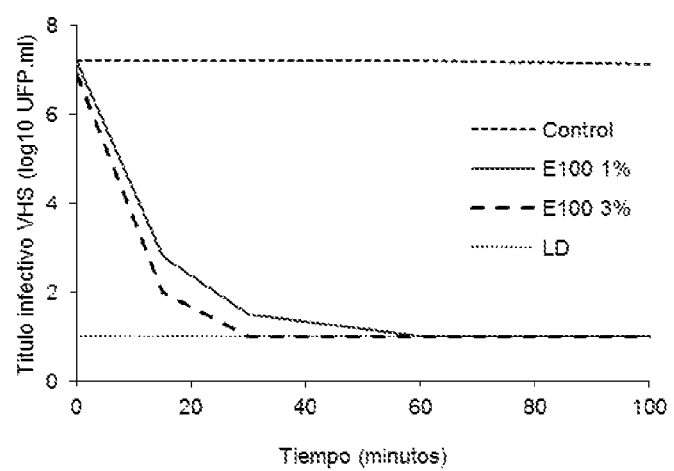

ANTIVIRAL PHARMACEUTICAL COMPOSITION FOR TOPICAL USE

RELATED APPLICATIONS

This application is the US national phase application of international application number PCT/ES2016/070365, filed 13 May 2016, which designates the US and claims priority to Argentine Application P20150101519 filed 15 May 2015, the contents of each of which are hereby incorporated by reference as if set forth in their entireties.

FIELD OF THE INVENTION

The present invention relates to a pharmaceutical formulation for topical use, as a gel or a liquid, of an antiviral effect.

STATE OF THE ART

Viruses are infectious agents composed of proteins and nucleic acids. Some types of viruses also have a lipid envelope derived from the plasmatic membrane of the host cell infected by the virus itself. This type of viruses is known as enveloped viruses.

There a considerable number of enveloped viruses, among which the families of Herpesvirus, Flavivirus, Rhabdovirus, Paramixoviridae, Rotavirus among others, can be mentioned.

Two general types of viruses called Type 1 and Type 2 can be described within the Herpes Virus family. Type 1 infections frequently occur during infancy or childhood. Infection is caused by direct contact with infected persons. As a consequence of the infection, Herpes Simplex Virus Type 1 causes small, clear, fluid-filled blisters that most often occur on the lips, while on the face it occurs as swollen and painful structures that heal spontaneously after 5-7 days without leaving new scars. It is known that such infections tend to reappear with time. Less frequently, Herpes Virus Type 1 infections occur in the genital area. Type 1 may also develop in wounds on the skin and mucous membranes.

Herpes Simplex virus Type 2 usually results in genital ulcers. Most people become infected with Herpes Type 2 after sexual contact with an infected person. Several estimations indicate that the virus affect 400 million people around the world.

Herpes Simplex Type 2 usually results in sores on the buttocks, penis, vagina or cervix, between two and twenty days after the sexual contact with the infected person. The virus is most frequently transmitted by sexual contact, even though Herpes Type 2 can occur in locations other than the genital area, generally below the waist.

Several topical antiviral agents have been used for the treatment of such infections, in particular idoxuridine in the early 70s, those compounds containing zinc salts and solutions of dimethyl sulfoxide at 75% and more recently antivirals such as acyclovir, ganciclovir, etc.

Persons who take acyclovir daily often have reduced herpes attacks and have achieved the absence of symptoms or lesions.

Even though there is no known cure for herpes, clinical studies are now being developed to attempt to reduce or possibly eliminate outbreaks. There is a continuous need to mitigate the effects of herpes.

Acyclovir and ganciclovir, both nucleosides analogues which behave as powerful virustatic agents that prevent virus replication, must be specially mentioned among the compounds which prevent Herpes Simplex Virus replication.

According to some studies, the concentrations of intracellular triphosphate ganciclovir are approximately ten-fold higher than those of acyclovir, and these values decrease more slowly, with a mean life of more than 24 hours.

Acyclovir is a nucleoside analogue approved in 1982, which is used in the systemic or topical treatment of Herpes Simplex Virus (HSV), varicella and herpes zoster virus.

The currently available topical formulations of acyclovir are creams and ointments. Cream formulations for the treatment of cold sores, seem to be more effective than ointments. Acyclovir has a remarkable antiviral activity on Herpes Simplex infections, and it has been described to present low toxicity.

However, the constraints to the topical use of acyclovir in the treatment of recurrent HSV skin infections have been documented. In fact, many common topical formulations does not guarantee a reliable and proper penetration of the active principle through the skin. In addition, conventional formulations such as creams, are not water resistant. Therefore, saliva washes them away progressively after they are applied. Clinical trials have proved that acyclovir cream is not much more efficient than placebo: recovery mean time from herpes lesions with acyclovir is 4.3 days, compared with 4.8 days with placebo.

A research developed and published in the Int. J. Pharm Compuesto 2000 January/February;-4-(1):-(59), a formulation of acyclovir cream combined with lidocaine, one of the most frequently used local anesthetics was disclosed. However, the analgesic effect of such combination seems to be of a secondary importance compared with acyclovir cream. This could be probably due to the fact that cream formulations do not allow the optimal penetration of active ingredients. Therefore, there is a need to improve topical formulations of acyclovir for the treatment of oral herpes.

Recently, in 2008, Smith Jeffrey, filed a patent in the U.S. Pat. No. 7,462,369 called "Anti-viral compositions and methods of making and using the anti-viral compositions". Antiviral compositions contain at least two active ingredients containing a zinc compound and an antioxidant, which can reduce and/or prevent skin lesions associated with viral infections and on the other hand it mentions that such formulation could mitigate the transmission of the virus. In addition to the active ingredients already mentioned such as zinc and antioxidants, the anti-viral compositions optionally contain a vehicle or pharmaceutical carrier to improve penetration of both active ingredients into an infected human and animal. According to the author, the anti-viral compositions may be topically applied to areas of concern on an infected subject, such as on the skin and/or mucous membranes, or administered orally, enterically, intravenously, intraperitoneally, or by injection.

No patent documents describing the present invention or which hint reaching it have been found.

BRIEF DESCRIPTION OF THE FIGURES

FIG. 1: Reduction of the infective titre of Herpes Simplex Virus on Hep-2 cells by treating the viral inoculum with the formulation of Example 1

BRIEF DESCRIPTION OF THE INVENTION

The antiviral pharmaceutical composition for topical use against those viruses of a lipid envelope, which is the object of the present invention, comprises as active ingredients a cationic copolymer containing tertiary amine groups, preferably a derivative of acrylic and more preferably Poly(butyl methacrylate-co-(2-dimethylaminoethyl)methacrylate-co-methyl methacrylate) 1:2:1, preferably in a concentration of between 0.1 and 5% by weight, more preferably between 0.5 and 3%, and more preferably between 1 and 2%; and a cationic surfactant containing quaternary ammonium groups, preferably cetylpyridinium chloride in a concentration of between 0.1 and 2% by weight, preferably between 0.3 and 0.5%. Additionally, said formulations of the invention optionally comprises an agent that facilitates the passage through the skin, which contains sulfur groups, preferably dimethyl sulfoxide in a concentration of between 2 and 35% by weight, preferably between 5 and 20%, more preferably between 8 and 15%; a cationic polymer of a high molecular weight to contribute the necessary viscosity to allow longer residence time on the area where it was applied, preferably polyquaternium 10 (No CAS: 81859-24-7); and an anesthetic for local use, selected from the group comprised by lidocaine, xylocaine, bupivacaine, tetracaine, mepivacaine, prilocaine, butacaine, procaine, ropivacaine and mixtures thereof, preferably lidocaine at a concentration of between 1 and 15% by weight, preferably between 2 and 10%, more preferably between 4 and 8% by weight.

DETAILED DESCRIPTION OF THE INVENTION

The present invention provides anti-viral compositions for topical use, which in addition to neutralizing viruses with lipid envelope may have mitigation effects on the pain caused by viral infections.

The anti-viral compositions of the present invention contain at least two active ingredients: on the one hand a cationic polymer such as poly (butyl methacrylate-co-(2-dimetilaminoeetil) methacrylate-co-methyl methacrylate) 1:2:1 (CAS: 24938-16-7), INCI name: Acrylates/Copolymer dimethylaminoethyl methacrylate, and on the other hand a cationic surfactant such as cetyl piridinino chloride (CPC). CPC also has properties to facilitate the passage of molecules through skin, as what happens with dimethylsulfoxide compound, a property which is known as "transdermal enhancers". In another formulation of the invention, in addition to these same compounds, also comprises an anesthetic so as to minimize the pain caused by the infection itself.

The anti-viral compositions of the present invention may be topically applied on areas of concern of an infected individual, such as skin and/or mucous membranes. In addition to poly (butyl methacrylate-co-2-dimethylaminoethyl) methacrylate-co-methyl methacrylate) 1:2:1 and of CPC, the anti-viral compositions of the present invention optionally contain a vehicle or carrier, such as a bioadhesive polymer, to keep for a longer time both active ingredients on the viral lesion to be treated.

The anti-viral composition of the present invention contains two active ingredients, which in their preferred embodiment are: the cationic polymer poly(butyl methacrylate-co-2 dimethylaminoethyl)methacrylate-co-methyl methacrylate) 1:2:1, and the surfactant cetylpyridinium chloride; also it optionally presents a carrier or facilitator for the skin passage as dimethyl sulfoxide, a cationic polymer which generates viscosity and bioadhesiveness to the tissue and optionally an efficient quantity of at least one analgesic. Analgesics are used to relieve pain and or discomfort due to the symptoms of the viral infection. The anti-viral compositions of the present invention may optionally contain one or more viscosifying agents with bioahesive properties such as cationic polymers, among which Poliquaternium-10 (No CAS 81859-24-7) can be mentioned.

EXAMPLES

Example 1—Pharmaceutical Formulation without Anesthetics

| Components expressed in gr/100 gr | |
|---|---|
| Poly(butyl methacrylate-co-(2-dimethylaminoethyl) methacrylate-co-methyl methacrylate) 1:2:1 | 1.00 |
| Cetylpyridinium chloride | 0.30 |
| Dimethyl Sulfoxide | 10 |
| Poliquaterniunn-10 | 1.5 |
| Water | 87.2 |

Example 2—Pharmaceutical Formulation with Anesthetics

| Components expressed in gr/100 gr | |
|---|---|
| Poly(butyl methacrylate-co-(2-dimethylaminoethyl) methacrylate-co-methyl methacrylate | 1.00 |
| Cetylpyridinium chloride | 0.30 |
| Dimethyl Sulfoxide | 10 |
| Lidocaine | 4 |
| Polyquaterniunn-10 | 1.5 |
| Water | 83.2 |

The formulations in Examples 1 and 2 when applied twice a day on ulcerations caused by Herpes Virus heal such ulcerations by the second day.

Example 3: Trial on Antiviral Activity Against Herpes Simplex I Using Cultured Cells FIG. 1 shows the reduction of the infective titre of Herpes Simplex Virus on Hep-2 cells by treating the viral inoculum with the formulation of Example 1 of the present invention. Where LD is the Detection Limit of the methodology of the analysis.

Description of the Trial:

Aliquots of 0.9 ml of a herpes virus suspension (infective titre $1\times10^7$) were treated with 0.1 ml of a solution of the formulation in Example 1 of 10% (final concentration in the sample: 1%). Samples were incubated for periods of varying lengths, after which the formulation in Example 1 was removed from the medium using a cationic exchange column. A virus processing control was also performed, in which 0.9 ml of the virus were treated with 0.1 ml of the same medium of the suspension, incubated for the longest period tested and passed through the exchange column.

Infective titre determination of each sample was performed on monolayers of cells Hep-2 at 90% grown to confluence on multiple plaques of 96 wells seeded 24 h before the test was performed.

The culture medium was removed, cells were washed once with PBS and incubated with 50 µl of each dilution (serial dilutions by 10 factor of each aliquot) at 37° C. for 1 hour.

All determinations were performed in quadruplicate. Inocula were removed and completed with cultured medium.

The infective titre was determined by the appearance of the cythopathic effect at 48 h, and it was calculated performing the Reed-Muench analysis.

These tests were also performed with the polymer formulated according to Examples 1 and 2, obtaining similar results. The remaining components of the formulation do not affect the polymer activity.

Example 4—Test of Skin Irritation of the Antiviral Formulation of the Present Invention For the evaluation of the potential irritating activity of the antiviral formulation of the present invention, the following test was performed: Six albino rabbits of approximately 3 Kg each were subjected to fur cut of their back, over a definite area of approximately 10 by 10 cm. The three Control Rabbits received an aqueous solution of a similar viscosity (Carboxymethylcellulose 1%), whereas the formulation in Example 2 was applied to Problem Rabbits.

In each case, Control and Problem, a dose of 1 ml of each solution was applied, distributed all over the skin prepared for testing. This treatment was carried out every 4 hours for 7 days. The appearance of signs of skin irritation, defined as the occurrence of erythema (redness) or swelling of the treated area, were evaluated every 24 hours for 7 days.

Results showed that the Problem Rabbits treated with the antiviral formulations or Example 2, like the rabbits of the Control Group, did not show skin irritation symptoms.

The invention claimed is:

1. An antiviral pharmaceutical composition for topical use against viruses with a lipid envelope, comprising active agents; a facilitating agent; and a cationic polymer, wherein the active ingredients consist of a cationic copolymer containing tertiary amine groups, and a cationic surfactant containing quaternary ammonium groups; wherein the facilitating agent for facilitating passage through skin includes sulfur groups; and wherein the cationic polymer contributes necessary viscosity to allow longer residence time on an applied area and comprises polyquaternium 10.

2. The antiviral pharmaceutical composition according to claim 1, further comprising an anesthetic for local use.

3. The antiviral pharmaceutical composition according to claim 1, wherein said cationic copolymer comprises an acrylic derivative.

4. The antiviral pharmaceutical composition according to claim 1, wherein said cationic copolymer comprises poly(butylmethacrylate-co-2-dimethylaminoethyl)methacrylate-co-methyl methacrylate) 1:2:1.

5. The antiviral pharmaceutical composition according to claim 1, wherein said cationic copolymer is present at a concentration of between 0.1 and 5% by weight of said antiviral pharmaceutical composition.

6. The antiviral pharmaceutical composition according to claim 1, wherein said cationic copolymer is present at a concentration of between 0.5 and 3% by weight of said antiviral pharmaceutical composition.

7. The antiviral pharmaceutical composition according to claim 1, wherein said cationic copolymer is present at a concentration of between 1 and 2% by weight of said pharmaceutical composition.

8. The antiviral pharmaceutical composition according to claim 1, wherein said cationic surfactant containing quaternary ammonium groups comprises cetylpyridinium chloride.

9. The antiviral c pharmaceutical composition according to claim 1, wherein said cationic surfactant containing quaternary ammonium groups is present at a concentration of between 0.1 and 2% by weight of said antiviral pharmaceutical composition.

10. The antiviral pharmaceutical composition according to claim 1, wherein said cationic surfactant containing quaternary ammonium groups is present at a concentration of between 0.3 and 0.5% by weight of said antiviral pharmaceutical composition.

11. The antiviral pharmaceutical composition according to claim 1, wherein said facilitating agent comprises dimethylsulfoxide in a concentration of between 2 and 35% by weight of said antiviral pharmaceutical composition.

12. The antiviral pharmaceutical composition according to claim 1, wherein said facilitating agent comprises dimethylsulfoxide in a concentration of between 5 and 20% by weight of said antiviral pharmaceutical composition.

13. The antiviral pharmaceutical composition according to claim 1, wherein said facilitating agent comprises dimethylsulfoxide in a concentration of between 8 and 15% by weight of said antiviral pharmaceutical composition.

14. The antiviral pharmaceutical composition according to claim 2, wherein said anesthetic for local use is selected from the group consisting of lidocaine, xylocaine, bupivacaine, tetracaine, mepivacaine, prilocaine, butacaine, procaine, ropivacaine and mixtures thereof, and is present at a concentration of between 1 and 15% by weight of said antiviral pharmaceutical composition.

15. The antiviral pharmaceutical composition according to claim 2, wherein said anesthetic for local use is selected from the group consisting of lidocaine, xylocaine, bupivacaine, tetracaine, mepivacaine, prilocaine, butacaine, procaine, ropivacaine and mixtures thereof, and is present at a concentration of between 2 and 10% by weight of said antiviral pharmaceutical composition.

16. The antiviral pharmaceutical composition according to claim 2, wherein said anesthetic for local use is selected from the group consisting of lidocaine, xylocaine, bupivacaine, tetracaine, mepivacaine, prilocaine, butacaine, procaine, ropivacaine and mixtures thereof, and is present at a concentration of between 4 and 8% by weight of said antiviral pharmaceutical composition.

17. A method for treating a virus of a lipid envelop comprising administering a therapeutically effective amount of the antiviral pharmaceutical composition of claim 1, to a subject thereof.

18. A method for treating Herpes Simplex Virus (HSV) varicella, or herpes zoster virus, said method comprising administering a therapeutically effective amount of the antiviral pharmaceutical composition of claim 1, to a subject in need thereof.

* * * * *